United States Patent [19]

Holm

[11] 4,145,209

[45] Mar. 20, 1979

[54] MULTICOMPONENT FRUIT ABSCISSION COMPOSITIONS

[75] Inventor: Robert E. Holm, Painesville, Ohio

[73] Assignee: Diamond Shamrock Corporation, Cleveland, Ohio

[21] Appl. No.: 766,382

[22] Filed: Feb. 7, 1977

Related U.S. Application Data

[63] Continuation-in-part of Ser. No. 603,454, Aug. 11, 1975, abandoned.

[51] Int. Cl.² ............................................. A01N 5/00
[52] U.S. Cl. .......................................... 71/92; 71/74
[58] Field of Search .................................... 71/92, 74

[56] References Cited

U.S. PATENT DOCUMENTS 3,663,199  5/1972  Cooper ................................... 71/74

Primary Examiner—Catherine L. Mills
Attorney, Agent, or Firm—Stuart L. Melton

[57] ABSTRACT

A composition comprising two compounds from the group cycloheximide, 5-chloro-3-methyl-4-nitro-1H-pyrazole and glyoxal dioxime and optionally including an additive compound capable of enhancing the activity of the composition is a synergistic combination capable of promoting fruit, especially citrus fruit, abscission when applied to trees bearing same.

4 Claims, No Drawings

MULTICOMPONENT FRUIT ABSCISSION COMPOSITIONS

CROSS-REFERENCE TO RELATED APPLICATION

This application is a continuation-in-part application of copending application Ser. No. 603,454, filed on Aug. 11, 1975 now abandoned.

BACKGROUND OF THE INVENTION

The desirability of facilitating the harvest of various agricultural crops, especially fruit crops such as citrus fruits, is readily apparent. A number of chemical compounds capable of promoting fruit abscission has been proposed, which compounds serve to reduce the pull force necessary to remove mature fruit from the tree or plant, thereby rendering mechanical harvesting possible. Few of these compounds, however, have found practical utility, mainly owing to their tendency, when used in effective amounts, to register undesirable side effects.

Several compounds are currently in use or under test as citrus fruit abscission agents. One such compound is cycloheximide, i.e., 3(2-[3,5-dimethyl-2-oxocyclohexyl]-2-hydroxyethyl) glutarimide. This use is described more fully in U.S. Pat. No. 3,663,199. While the compound is indeed effective in reducing the pull force necessary to remove citrus fruit from trees, its use has been seasonally limited on some citrus varieties (e.g., Valencia oranges) since its application in an amount effective to cause the desired abscission, can also result in damage to immature fruit and cause leaf and bloom drop.

Two other such compounds are 5-chloro-3-methyl-4-nitro-1H-pyrazole and glyoxal dioxime. These compounds are again effective but, when used in large amounts, excessive rind damage occurs, leading to post harvest disease and/or an "off" taste in fruit juices made therefrom.

STATEMENT OF THE INVENTION

Therefore, it is an object of the present invention to provide a composition and method of employing same capable of causing abscission of mature fruit, while reducing undesirable side effects.

This and other objects of the present invention will become apparent to those skilled in the art from the specification and claims that follow.

There has now been found a fruit abscission composition comprising two compounds from the group cycloheximide, 5-chloro-3-methyl-4-nitro-1H-pyrazole, and glyoxal dioxime. The compositions are employed as fruit abscission agents by applying same to a fruit locus in an abscission-promoting amount and, subsequently, applying sufficient force on said fruit to remove same.

Moreover, in accordance with certain preferred embodiments of the present invention, it has also been found that the effectiveness of the aforementioned fruit abscission agents can be still further enhanced by the inclusion of various compounds which are completely inactive in promoting fruit abscission when employed alone. Exemplary of such compounds are N-[(trichloromethyl)thio]phthalimide, cis-N-[(trichloromethyl)thio]-4-cyclohexene-1,2-dicarboximide, cis-N-[(1,1,2,2-tetrachloroethyl)thio]-4-cyclohexene-1,2-dicarboximide, ferric dimethyldithiocarbamate, ethylenebisdithiocarbamate manganese, ethylenebisdithiocarbamate zinc, methyl-1-(butylcarbamoyl)-2-benzimidazolecarbamate, or tetrachloroisophthalonitrile.

Such compositions allow use of lesser amounts of the individual compounds, thereby reducing the undesirable side effects which are attributed to each of said compounds. Additionally, at most concentrations, the combination of compounds acts synergistically in causing fruit abscission.

DESCRIPTION OF THE PREFERRED EMBODIMENTS

Throughout the specification and claims, the term "fruit" is used to define a variety of agricultural products, the removal of which from the parent plant or tree (hereinafter, tree) may be promoted by the use of an abscission agent. Typically included are oranges, lemons, grapefruit, limes, olives, cherries, apples, pecans, and walnuts. Especially important, and referred to particularly hereinafter, are the citrus fruits.

The composition comprises two compounds from the group cycloheximide, 5-chloro-3-methyl-4-nitro-1H-pyrazole, and glyoxal dioxime. Presently preferred is the combination of cycloheximide and 5-chloro-3-methyl-4-nitro-1H-pyrazole. When the composition comprises cycloheximide and 5-chloro-3-methyl-4-nitro-1H-pyrazole, the former compound will preferably constitute from 2 to 40 percent, by weight, of the total of the two compounds. When the combination is cycloheximide plus glyoxal dioxime, the cycloheximide will preferably constitute from 1.5 to 15 percent of the total. 5-Chloro-3-methyl-4-nitro-1H-pyrazole will preferably constitute from 25 to 75 percent of the total of said pyrazole and glyoxal dioxime.

The composition is generally applied to the fruit as an aqueous spray, this being most convenient and economical, although dusting or other methods of application are possible. Preparation of the aqueous formulation merely requires the dispersion or emulsification of the compounds in the stated proportions at concentrations of from 5 to 15 ppm cycloheximide, 25 to 250 ppm 5-chloro-3-methyl-4-nitro-1H-pyrazole, and 50 to 300 ppm glyoxal dioxime. A nonphytotoxic surfactant, such as polyoxyethylated sorbitan monolaurate, is generally employed to achieve the formulation.

In addition to the two compounds, the composition may also contain any of the variety of compounds which, while inactive in causing fruit abscission themselves, by some mechanism (presumably an increased internal ethylene production) are able to promote the effectiveness of true fruit abscission agents. Thus, these compounds can be employed to lessen the concentration of fruit abscission agents in the formulation, thereby further reducing undesirable side effects, or they will enhance fruit abscission activity at the same concentration of abscission agent. The compounds which may be employed in combination with the two abscission agents are: N-[(trichloromethyl)thio] phthalimide, cis-N[(trichloromethyl)thio]-4-cyclohexene-1,2-dicarboximide, cis-N-[(1,1,2,2-tetrachloroethyl)thio]-4-cyclohexene-1,2-dicarboximide, ferric dimethyldithiocarbamate, ethylenebisdithiocarbamate manganese, ethylenebisdithiocarbamate zinc, methyl-1-(butylcarbamoyl)-2-benzimidazolecarbamate, or tetrachloroisophthalonitrile. These compounds are generally employed at a ratio of from 1 to 20 parts per part of the combination of cycloheximide, 5-chloro-3-methyl-4-nitro-1H-pyrazole, or glyoxal dioxime. Thus, they will be present in the aqueous formulation within the range of from 50 to 1000 ppm.

Based upon effectiveness in promoting fruit abscission as determined by a reduction in the pull force required to remove fruit from the stem and an increase in natural fruit fall as well as the minimization of undesirable side effects, a particularly preferred composition according to the present invention comprises cycloheximide, 5-chloro-3-methyl-4-nitro-1H-pyrazole and tetrachloroisophthalonitrile in admixture. Depending upon formulation variations, application rates and schedules as well as fruit varieties involved, the relative amounts of the foregoing components will generally range between about 2.5 to 15 ppm, 25 to 250 ppm and 50 to 1000 ppm, respectively. However, balancing abscission effectiveness and economic considerations, concentration levels may desirably be maintained between about 2.5 to 5 ppm, 50 to 150 ppm, and 125 to 250 ppm, respectively.

When the fruit has reached substantial maturity, the abscission composition is applied, generally 3 to 10 days prior to the desired harvesting date, by spraying the fruit locus, although the entire tree may be treated for convenience. Application may be by low volume spray, to run-off, or otherwise as desired. Harvesting is then accomplished by exerting sufficient force on the fruit to remove it from the tree. Often, the weight of the fruit alone will cause it to fall from the tree, demonstrating a pull force of less than 0.5 kg. More typically, some positive force must be applied, such as mechanical shaking or from air or water guns.

In order that those skilled in the art may more readily understand the present invention and certain preferred embodiments by which it may be carried into effect, the following specific examples are afforded.

EXAMPLE 1

Aqueous formulations containing the amounts of cycloheximide (CHI) and 5-chloro-3-methyl-4-nitro-1H-pyrazole (pyrazole) shown in Table I are prepared. Branches of Hamlin orange trees containing from 20 to 30 mature fruit are treated to run-off with the aqueous formulation. Seven days later, the force necessary to remove the fruit from the stem is measured. Each result in Table I is an average of three replicate treatments.

TABLE I

| CHI (ppm) → | 0 | | 5 | | 10 | | 15 | |
|---|---|---|---|---|---|---|---|---|
| Pyrazole (ppm) ↓ | PF[1] | FF[2] | PF | FF | PF | FF | PF | FF |
| 0 | 7.3 | 0 | 4.4 | 0 | 3.3 | 1 | 2.3 | 0 |
| 25 | 7.3 | 0 | 1.9 | 12 | <0.5 | 100 | 0.9 | 10 |
| 50 | 4.4 | 0 | 1.4 | 0 | <0.5 | 100 | 0.9 | 85 |
| 100 | 3.3 | 25 | <0.5 | 100 | <0.5 | 100 | 0.9 | 90 |
| 200 | 1.5 | 75 | <0.5 | 100 | <0.5 | 100 | <0.5 | 100 |

[1]Pull force, in kg., to remove fruit from stem
[2]% fruit fall, without added force In all instances, a beneficial effect is observed with the combination of compounds. Further, the combination is synergistic up to 100% efficacy.

EXAMPLE 2

Aqueous formulations are again prepared employing the amounts of cycloheximide and glyoxal dioxime (dioxime) indicated in Table II. In this instance, branches of Valencia orange trees are selected, each bearing from 20 to 30 mature fruit, and treated to run-off. Seven days later, the force necessary to remove the fruit from the stem is measured with the results shown in Table II. Each result is an average of three replicate treatments.

TABLE II

| CHI (ppm) → | 0 | | 5 | | 10 | | 15 | |
|---|---|---|---|---|---|---|---|---|
| Dioxime (ppm) ↓ | PF[1] | FF[2] | PF | FF | PF | FF | PF | FF |
| 0 | 8.8 | 0 | 5.5 | 0 | 3.9 | 0 | 3.1 | 0 |
| 100 | 8.8 | 0 | 5.2 | 0 | 2.5 | 0 | 2.0 | 0 |
| 200 | 7.2 | 0 | 2.1 | 2 | <0.5 | 1 | <0.5 | 6 |
| 300 | 4.7 | 0 | <0.5 | 2 | <0.5 | 2 | <0.5 | 13 |

[1]Pull force, in kg., to remove fruit from stem
[2]Numerical fruit fall, without added force Again, a synergistic effect up to 100% efficacy is demonstrated. By comparison, use of sufficient cycloheximide alone (i.e., 20 ppm) to achieve a pull force of less than 0.5 kg results in an 80% mature leaf fall and flush drop and a 100% bloom drop.

EXAMPLE 3

The procedure and conditions of Example 2 are repeated, substituting the indicated quantity of 5-chloro-3-methyl-4-nitro-1H-pyrazole for cycloheximide. Results are shown in Table III.

TABLE III

| Pyrazole (ppm) → | 0 | | 100 | | 200 | | 300 | |
|---|---|---|---|---|---|---|---|---|
| Dioxime (ppm) ↓ | PF[1] | FF[2] | PF | FF | PF | FF | PF | FF |
| 0 | 8.8 | 0 | 7.5 | 0 | 3.8 | 1 | 1.5 | 16 |
| 100 | 8.8 | 0 | 6.4 | 0 | 2.4 | 6 | <0.5 | 10 |
| 200 | 7.2 | 0 | 4.6 | 0 | 1.9 | 2 | <0.5 | 20 |
| 600 | 4.7 | 0 | 3.5 | 1 | <0.5 | 11 | <0.5 | 25 |

[1]Pull force, in kg., to remove fruit from stem
[2]Numerical fruit fall, without added force Again, the synergistic effect is noted.

EXAMPLE 4

Aqueous formulations containing the amounts of cycloheximide, 5-chloro-3-methyl-4-nitro-1H-pyrazole and tetrachloroisophthalonitrile (TCIPN) shown in Tables IV and V below are prepared and evaluated with respect to fruit abscission activity on different seasonal varieties of oranges.

TABLE IV

Comparison of Individual Abscission Agents and Combinations of Same with TCIPN in Whole Tree Tests[1]

| | No. Trees | | | PYRAZOLE or (CHI) | | | PYRAZOLE + CHI + TCIPN Combinations | | |
|---|---|---|---|---|---|---|---|---|---|
| Test No. | Per Treatment | Test Total | Date Applied | Rate (ppm) | PF[2] (kg) | Fruit drop[3] (no./tree) | Rate (ppm) | PF[2] (kg) | Fruit drop[3] (no./tree) |
| | | | | Pineapple | | | | | |
| 1 | 15 | 90 | 1/22 | 250 | <0.7 | | 650 150+10+500 | <0.5 | 750 |
| | | | | Hamlin | | | | | |
| 2 | 10 | 90 | 1/26 | 150 | 3.2 | | 350 100+5+250 | <0.9 | 450 |
| | | | | | | | 100+5+0 | 1.2 | 250 |

TABLE IV-continued

Comparison of Individual Abscission Agents and Combinations of Same with TCIPN in Whole Tree Tests[1]

| | No. Trees | | | Treatments applied | | | | | |
|---|---|---|---|---|---|---|---|---|---|
| | | | | PYRAZOLE or (CHI) | | | PYRAZOLE + CHI + TCIPN Combinations | | |
| Test No. | Per Treatment | Test Total | Date Applied | Rate (ppm) | PF[2] (kg) | Fruit drop[3] (no./tree) | Rate (ppm) | PF[2] (kg) | Fruit drop[3] (no./tree) |
| | | | | Hamlin | | | | | |
| 3 | 40 | 520 | 2/5 | 100 | 1.9 | 330 | 50+10+500 | 1.0 | 669 |
| | | | | | | | 75+5+250 | 0.9 | 679 |
| 4 | | | | (5) | (3.6) | (54) | 0+5+250 | 2.6 | 225 |
| 5 | | | | (10) | (2.8) | (158) | 0+10+500 | 2.0 | 248 |
| 6 | | | | (15) | (4.7) | (263) | 0+15+750 | 1.2 | 347 |
| 7 | 40 | 520 | 2/11 | 25 | 3.8 | 210 | 25+5+250 | 1.7 | 896 |
| 8 | | | | (5) | (3.4) | (156) | 25+5+0 | 2.4 | 633 |
| 9 | | | | (10) | (2.9) | (208) | 0+10+500 | 1.7 | 277 |
| 10 | | | | 100 | 1.9 | 630 | | | |
| 11 | 40 | 320 | 2/20 | 25 | 2.1 | 91 | 25+2.5+125 | 1.5 | 404 |
| 12 | | | | (2.5) | (1.5) | (124) | 25+2.5+0 | 2.7 | 423 |
| 13 | | | | 50 | 1.5 | 212 | 50+2.5+125 | <0.5 | 448 |
| | | | | | | | 50+2.5+0 | 1.5 | 500 |

[1]Treatments applied in commercial groves using 8 to 10 gallons/tree.
[2]PF = Pull force. Data taken on at least 5 trees/treatment - 10 to 20 readings/tree. Average control (untreated) for the test period was 6.9 kg with negligible fruit drop.
[3]Cumulative total at 7 days.

TABLE V

Comparison of Individual Abscission Agents and Combinations of Same with TCIPN in Whole Tree Tests[1]

| | No. Trees | | | Treatments applied | | | | | |
|---|---|---|---|---|---|---|---|---|---|
| | | | | PYRAZOLE | | | PYRAZOLE + CHI + TCIPN Combinations | | |
| Test No. | Per Treatment | Test Total | Date Applied | Rate (ppm) | PF[2] (kg) | Fruit drop[3] (no./tree) | Rate (ppm) | PF[2] (kg) | Fruit drop[3] (no./tree) |
| 1 | 2 | 14 | 3/8 | 100 | 4.7 | 5 | 100+5+0 | 2.0 | 86 |
| | | | | | | | 100+5+250 | 1.5 | 211 |
| 2 | 2 | 12 | 3/12 | 250 | 1.9 | 83 | 100+5+0 | 3.6 | 40 |
| | | | | | | | 100+5+250 | 1.8 | 271 |
| 3 | 2 | 14 | 3/29 | 250 | 2.5 | 182 | 100+5+0 | 2.9 | 39 |
| | | | | | | | 100+5+250 | 1.5 | 158 |
| | | | | | | | 100+10+0 | 2.2 | 140 |
| | | | | | | | 100+10+500 | 1.3 | 238 |
| 4 | 2 | 26 | 4/12 | 250 | 1.7 | 221 | 100+5+0 | 2.6 | 53 |
| | | | | | | | 100+5+250 | 1.7 | 152 |
| 5 | 2 | 28 | 4/27 | 250 | 3.3 | 74 | 200+5+0 | 3.4 | 87 |
| | | | | | | | 200+5+250 | 2.5 | 215 |
| 6 | 9 | 45 | 4/30 | 250 | 3.1 | 79 | 150+5+250 | 2.7 | 59 |
| 7 | 2 | 18 | 5/10 | 250 | 4.1 | 110 | 200+5+250 | 2.0 | 276 |
| 8 | 3 | 15 | 5/18 | 250 | 2.2 | 683 | 200+5+250 | 1.4 | 730 |
| 9 | 2 | 12 | 5/25 | 250 | 3.0 | 168 | 200+5+250 | 2.3 | 182 |
| 10 | 9 | 45 | 5/29 | 250 | 2.4 | 187 | 150+5+250 | 1.6 | 149 |
| 11 | 4 | 12 | 6/14 | 250 | 2.0 | 246 | 200+5+250 | 1.4 | 283 |

[1]Treatments applied to Valencia oranges in commercial groves.
[2]PF = Pull force - 10 readings/tree. Data were usually taken daily during the experiment. Values given are maximum loosening obtained with the treatment 3-7 days after application. Average control (untreated) for the test period was 8.8 kg with negligible fruit drop.
[3]Cumulative total at 7 days.

The fundamental basis for the synergistic responses and potentiation effects observed with combinations of cycloheximide and 5-chloro-3-methyl-4-nitro-1H-pyrazole as well as compositions comprising the foregoing and including an additive compound capable of enhancing the fruit abscission activity of the foregoing composition, such as tetrachloroisophthalonitrile, is presently believed to be due to the enhancement of internal fruit ethylene production. A direct correlation between the ability of a compound or composition to stimulate internal fruit ethylene production and its ability to facilitate fruit abscission has been confirmed. The compositions in accordance with the present invention induce significantly higher levels of internal fruit ethylene production than could be expected to be achieved according to the algebraic sum of the effects of individual chemicals from 2 to 7 days after treatment and, hence, the fruit removal force (force required to remove the fruit from the stem) is significantly lowered using the present compositions as indicated by the data in Tables IV and V above. Surprisingly, the compositions in accordance with the present invention not only enhance peak ethylene production which is important for initial loosening of the fruit, but also sustain higher ethylene levels for longer periods than the individual abscission agents which promotes extended abscission activity permitting prolonged harvesting. Ability of the present compositions to sustain higher ethylene levels over extended periods is thought to be entirely unexpected inasmuch as it has been found that fruit treated with cycloheximide or pyrazole-type abscission agents alone begin to retighten approximately 4 to 5 days after treatment with a concomitant increase in required fruit removal force making mechanical removal considerably more difficult. However, fruit treated with the compositions of the present invention remain sufficiently loose to permit harvesting up to 8 to 10 days after treatment which could be an extremely valuable delay, particularly if weather or equipment problems occur in the interim between treatment and harvest. Accordingly, by obtaining unexpected control over internal fruit ethylene production using the present compositions, one can control the degree and duration of fruit abscission to an extent that has not been possible with previously suggested abscission chemicals.

The fruit abscission compositions of the present invention not only evidence advantageous results with respect to enhanced fruit abscission activity while at the same time minimizing undesirable side effects such as damage to immature fruit, leaf and bloom drop, excessive rind damage, etc., but in addition, compared to individual abscission chemical usage, the compositions of the present invention require from 25% to 50% less abscission chemical per treatment resulting in significant cost savings.

I claim:

1. A fruit abscission composition comprising cycloheximide and glyoxal dioxime, wherein the amount of said cycloheximide in said composition is not in excess of about 20 ppm and said dioxime is present in an amount in excess of the amount of said cycloheximide.

2. A composition as in claim 1 wherein said cycloheximide is present in an amount ranging from about 2 to about 40 percent, by weight, of the total of said cycloheximide and said dioxime.

3. A method of harvesting fruit from a tree, which method comprises applying to the fruit locus an abscission promoting amount of a composition comprising cycloheximide in an amount not in excess of about 20 ppm and glyoxal dioxime, said dioxime being present in an amount in excess of the amount of said cycloheximide and subsequently applying sufficient force on said fruit to remove same.

4. The method as in claim 3 wherein application is to run-off of a formulation containing from about 2.5 to 15 ppm cycloheximide and about 50 to 300 ppm dioxime.

* * * * *